United States Patent
Bieder et al.

(10) Patent No.: US 11,592,413 B2
(45) Date of Patent: Feb. 28, 2023

(54) METHOD FOR DETERMINING A NICOTINE CONTENT IN A GAS MIXTURE

(71) Applicant: Robert Bosch GmbH, Stuttgart (DE)

(72) Inventors: Gudrun Bieder, Denkendorf (DE); Philipp Nolte, Gerlingen (DE); Chi Trung Ngo, Singapur (SG); Philipp Pfander, Herrenberg (DE)

(73) Assignee: ROBERT BOSCH GMBH, Stuttgart (DE)

( * ) Notice: Subject to any disclaimer, the term of this patent is extended or adjusted under 35 U.S.C. 154(b) by 43 days.

(21) Appl. No.: 17/373,044

(22) Filed: Jul. 12, 2021

(65) Prior Publication Data
US 2022/0018795 A1    Jan. 20, 2022

(30) Foreign Application Priority Data
Jul. 17, 2020   (DE) .......................... 102020208982.5

(51) Int. Cl.
*G01N 27/12*   (2006.01)
*G01N 33/00*   (2006.01)

(52) U.S. Cl.
CPC ....... *G01N 27/124* (2013.01); *G01N 33/0036* (2013.01)

(58) Field of Classification Search
CPC .. G01N 27/124; G01N 33/0036; G01N 27/12; G01N 27/125; G05D 23/19
See application file for complete search history.

(56) References Cited

U.S. PATENT DOCUMENTS

| | | | | |
|---|---|---|---|---|
| 4,012,692 A | * | 3/1977 | Eicker | G01N 27/124 422/98 |
| 2015/0272220 A1 | * | 10/2015 | Spin | A24F 40/60 131/329 |

(Continued)

FOREIGN PATENT DOCUMENTS

| | | |
|---|---|---|
| DE | 19639072 A1 | 3/1998 |
| DE | 102017206202 A1 | 10/2018 |
| EP | 2995938 A1 | 3/2016 |

OTHER PUBLICATIONS

Huang et al., "Gas Sensing Behavior of a Single Tin Dioxide Sensor Under Dynamic Temperature Modulation," Science Direct, Sensors and Actuators B 99, 2004, pp. 444-450.

(Continued)

*Primary Examiner* — Huy Q Phan
*Assistant Examiner* — Zannatul Ferdous
(74) *Attorney, Agent, or Firm* — Norton Rose Fulbright US LLP; Gerard Messina

(57) ABSTRACT

A method for determining a nicotine content in a gas mixture. The method includes exposing a metal oxide-based sensor to the gas mixture, applying a temperature profile over time to the metal oxide so that the temperature of the metal oxide, proceeding from a predetermined first temperature level, is brought to a predetermined second temperature level under controlled first transition conditions, and the temperature is brought from the second temperature level to a third predetermined temperature level under controlled second transition conditions, ascertaining a transient specific electrical resistance of the metal oxide at at least one certain point in time during the application with the temperature profile, and determining the nicotine content based on the (Continued)

ascertained resistance. A processing unit and a computer program product for carrying out the method are also described.

17 Claims, 2 Drawing Sheets

(56) References Cited

U.S. PATENT DOCUMENTS

| | | | |
|---|---|---|---|
| 2020/0209176 A1* | 7/2020 | Brueser | G01N 27/14 |
| 2021/0293733 A1* | 9/2021 | Ninos | G01N 33/0027 |
| 2022/0003702 A1* | 1/2022 | Ben Hamouda | G01N 27/02 |

OTHER PUBLICATIONS

Lin et al., "A Rapid and Novel Method for Predicting Nicotine Alkaloids in Tobacco Through Electronic Nose and Partial Least-Squares Regression Analysis," Anal. Methods, 2016, 8, pp. 1609-1617.

Julian et al., "Metal Oxide Semiconductor Based Electronic Nose as Classification and Prediction Instrument for Nicotine Concentration in Unflavoured Electronic Juice," 2018 4th International Conference On Science and Technology (ICST), Yogyakarta, Indonesia, 2018, pp. 1-5.

* cited by examiner

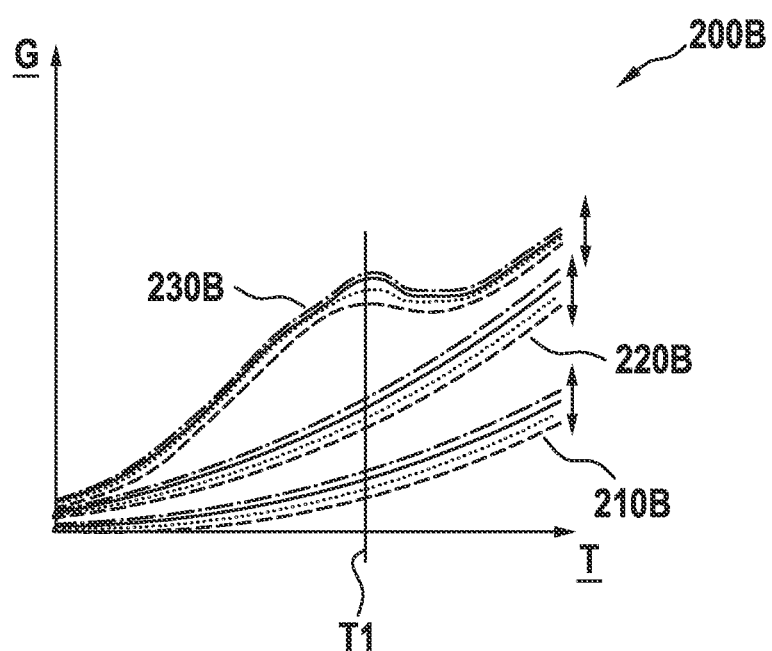

METHOD FOR DETERMINING A NICOTINE CONTENT IN A GAS MIXTURE

CROSS REFERENCE

The present application claims the benefit under 35 U.S.C. § 119 of German Patent Application No. DE 102020208982.5 filed on Jul. 17, 2020, which is expressly incorporated herein by reference in its entirety.

FIELD

The present invention relates to a method for determining a nicotine content in a gas mixture and to a processing unit and a computer program for carrying out the method.

BACKGROUND INFORMATION

European Patent Application No. EP 2 995 938 A1 describes a chemical sensor in which at least one layer of a metal oxide is situated between two electrodes, one or multiple heating element(s) being situated to heat the metal oxide layer to a predefined temperature according to a predefined temperature profile, and a control unit for controlling the heating elements, the control unit and the heating elements being designed in such a way that they heat the metal oxide layer when a measurement is initialized, that the layer temperature follows a temperature profile, including an activation period, during which the layer temperature is above a measuring temperature, prior to a measuring period, during which the layer temperature is at the measuring temperature, and the control unit deriving a concentration value of a gas compound from the resistance of the metal oxide layer as it was registered during the measuring time period.

SUMMARY

According to the present invention, a method for determining a nicotine content in a gas mixture and a processing unit and a computer program for carrying out the method, are provided. Advantageous embodiments are the present invention are disclosed herein.

Sensors which detect and evaluate the concentration of one or multiple component(s) of a gas mixture may be used for monitoring the adherence to limiting values, for example for an assessment of work atmospheres. For example, electrochemically operating sensors may be used for this purpose, which have a concentration-dependent potential, for example in an electrochemical half-cell.

Sensors based on metal oxides, whose electrical properties change as a function of the type and concentration of chemical compounds adsorbed or absorbed thereon, are also, in principle, possible. For example, metal oxide sensors, which respond with sensitivity to carbon monoxide, ammonia, or nitrogen dioxide, are commercially available. Sensors which are able to detect the concentration of volatile organic chemicals (VOC) in general are also offered.

Metal oxide sensors take advantage of the fact that gas components change the electrical resistance of a metal oxide layer by adsorption thereon or absorption therein. Since the influence of different gas components on the electrical conductivity or the electrical resistance is temperature-dependent, such measurements are carried out at a defined temperature by heating the metal oxide layer. In general, sensors are sensitive to more than just one component at a fixed temperature. When the metal oxide layer is exposed to the gas mixture, the individual components of the gas mixture cannot be directly inferred from the measured electrical resistance of the layer at only one temperature. To obtain more comprehensive information, metal oxide sensors may be operated at different temperatures, and the individual measured values, which are obtained at different temperatures, may be computed with one another.

Gas mixtures, as they are analyzed using the present invention, include a plurality of gases and/or substances dissolved in the mixture or transported by an uplift. It should be noted that, within the scope of the present invention, it is possible that gaseous substances, in the pure state, are not part of the corresponding gas mixture, or only to a small degree, even under the utilized conditions. A typical example in this connection is water: Even though water is liquid under standard conditions (e.g., 20° C., 101.3 kPa), it has a vapor pressure which cannot be ignored, so that it may be present in a gas mixture in a fraction which corresponds to a partial pressure below the corresponding vapor pressure, without condensing. This also applies analogously to other substances, for example so-called volatile organic compounds (VOC), which, as pure substances, may be solid or liquid under the given conditions, but when diluted are also stable in the gaseous state. Even other substances may be stable in the liquid or solid state under the given conditions, however, they may be present in the gas mixture in the form of an aerosol due to their small particle or droplet size. Within the scope of the present invention, accordingly not only mixtures made up exclusively of gaseous components, but also aerosols are referred to as gas mixtures.

When, in connection with the present invention, mention is made of an object having a temperature level, or being (present) at a temperature level, the particular temperature level is not characterized by an exact temperature, but shall be understood in such a way that a temperature is present which, even though it is essentially constant, is not unambiguously established, but rather is in a range around the particular indicated value. In particular, this refers to a temperature which is in a range of ±10% or ±10° C. around the indicated value. For example, a component which has a temperature level of 100° C. may have a temperature of 90° C. to 110° C.; however, the temperature of the component does not fluctuate within this range, but is essentially constant (for example, it fluctuates by no more than 2° C.)

Within the scope of the present invention, common names of chemical compounds, in particular, natural materials, in each case denote the naturally or most frequently occurring substance itself, as well as its stereoisomers and arbitrary mixtures thereof.

Unless information about mixture compositions in this description expressly describes something different, it refers in each case to the percent by volume of the corresponding component in the total volume of the mixture or to the partial pressure fraction of the particular component. Within the scope of the accuracy considered here, this is equivalent to the corresponding ratios with respect to the substance quantity.

The method according to an example embodiment of the present invention for determining a nicotine content in a gas mixture includes exposing a metal oxide-based sensor to the gas mixture, applying a temperature profile over time to the metal oxide so that the temperature of the metal oxide, proceeding from a predetermined first temperature level, is brought to a predetermined second temperature level under controlled first transition conditions, and the temperature is brought from the second temperature level to a third predetermined temperature level under controlled second transition conditions, ascertaining an electrical resistance of the metal oxide at at least one certain point in time during the application of the temperature profile, and determining the nicotine content based on the ascertained resistance. In this way, it is possible to measure the nicotine content of a gas mixture, in particular, of air, quickly and in an energy-saving manner, and to integrate the measurement easily into electronic circuits.

The electrical properties of the active material of the sensor vary as a function of the chemical surroundings of the respective metal and oxygen atoms in the material. To achieve a high sensitivity for components from gas mixtures, in general the surface of the active material is configured to be as large as possible to achieve an intensive exchange with the gas phase and achieve a high fraction of the material in exchange with the gas phase in the overall amount of the active material. The active material is thus advantageously provided as a porous matrix having an open pore system.

Advantageously, in accordance with an example embodiment of the present invention, the first and second transition conditions in each case encompass a transition duration and/or a temporal temperature progression of the respective temperature adjustment. In this way, the selectivity and sensitivity of the sensor are increased.

In particular, the transition duration is between 100 ms and 600 s, preferably between 1 s and 120 s, most preferably between 10 s and 90 s. This has proven to be particularly advantageous with respect to the selectivity of the sensor regarding nicotine and enables rapid sequences of measurements.

The temperature adjustment is preferably provided by resistance heating, a Carnot process, convection, ventilation and/or a Peltier effect. Depending on the operating surroundings, in this way it is possible to take advantage of suitable options for temperature adjustment, in particular, those which are available in the particular surroundings anyhow.

The first temperature level is preferably in a range of 200° C. to 400° C., in particular, of 250° C. to 350° C., the second temperature level is in a range of 0° C. to 100° C., in particular of 10° C. to 40° C., preferably of 15° C. to 35° C., and the third temperature level is in a range of 200° C. to 400° C., in particular of 300° C. to 400° C. These ranges enable a particularly effective measurement of nicotine, in particular, in gas mixtures including further components from the group of hydrogen sulfide, dimethyl disulfide, ethanol, and acetone.

The third temperature level advantageously corresponds to the first temperature level. In this way, the complexity during operation of the sensor is reduced since fewer different temperature levels have to be activated. In this way, a sequence of measurements may also take place very easily, only requiring switching between two temperature levels.

The at least one certain point in time is preferably in a time period in which the metal oxide experiences a temperature change or in which it is not present at any of the temperature levels. This considerably increases the selectivity of the sensor.

In accordance with an example embodiment of the present invention, the certain point in time is particularly preferably in a time period in which the temperature is being increased, in particular, in a partial time period in which the respective target temperature level, based on a difference between the starting temperature level and the target temperature level, is at least 70% achieved. This has proven to be particularly advantageous with respect to the selectivity of the sensor.

In accordance with an example embodiment of the present invention, the method advantageously furthermore includes repeating, in particular, cyclically, the application of the temperature profile. In this way, a development of the nicotine concentration in the gas mixture over time may be detected.

In accordance with an example embodiment of the present invention, the method particularly preferably then furthermore includes ascertaining a moving average of at least two consecutive determinations of the nicotine content. In this way, the reliability of the ascertained value increases considerably.

In accordance with an example embodiment of the present invention, the method advantageously furthermore includes analyzing at least one further component of the gas mixture, in particular, carbon monoxide, water vapor, volatile organic compounds (VOC), sulfurous compounds, such as hydrogen sulfide, and/or alcohol. For this purpose, at least one further sensor, which may also include a metal oxide as active material, may be used, if necessary. In this way, the accuracy of the determination of the nicotine content may be increased, for example using calibration curves, since cross influences may be recognized and taken into consideration. In addition, this enables a determination as to whether the nicotine content ascertained according to the present invention stems from a presently burning cigarette, or whether it is "cold" cigarette smoke (e.g., smoking in rooms which occurred temporally in the past or odor on clothing). It is also possible to distinguish emissions of a burning tobacco product from the emissions of vaporization apparatuses for nicotine-containing liquid preparations. In combination with an unspecific sensor which supplies results more quickly or enables shorter measuring intervals, additionally, at least subsequently, a time advantage during the detection of the point in time at which a nicotine release begins may be achieved.

A processing unit according to the present invention, e.g., a microcomputer including a metal oxide sensor, is configured, in particular from a programming point of view, to carry out a method according to the present invention.

An example embodiment of the present invention preferably uses at least one sensor including an active material (metal oxide), whose conductivity changes as a function of a nicotine content in an analyzed gas mixture. For example, the layer may predominantly include tungsten oxide or tin oxide, and the preferred temperature for reading out the resistance may be between 300° C. and 350° C. In the process, it was established that active materials having a monotonically increasing electrical conductivity as a function of the temperature in the passed-through temperature range with the applied temperature gradient are advantageous (robustness with respect to the other gases) compared to active materials having a local maxima of the electrical conductivity as a function of the temperature.

In addition, the implementation of a method according to the present invention in the form of a computer program or a computer program product having program code for carrying out all method steps is advantageous since this results in particularly low costs, in particular when an executing control unit is also used for additional tasks and is therefore present anyhow. Suitable data media for providing the computer program are, in particular, magnetic, optical, and electrical memories, such as hard disks, flash memories, EEPROMs, DVDs, and the like. It is also possible to download a program via computer networks (Internet, Intranet, and the like).

Further advantages and embodiments of the present invention are derived from the description herein and the figures.

The present invention is schematically shown based on one exemplary embodiment in the figures and is described hereafter with reference to the figures.

BRIEF DESCRIPTION OF THE DRAWINGS

FIGS. 2A and 2B show examples of sensor signals as they may be obtained within the scope of the present invention.

DETAILED DESCRIPTION OF EXAMPLE EMBODIMENTS

Figure 1:
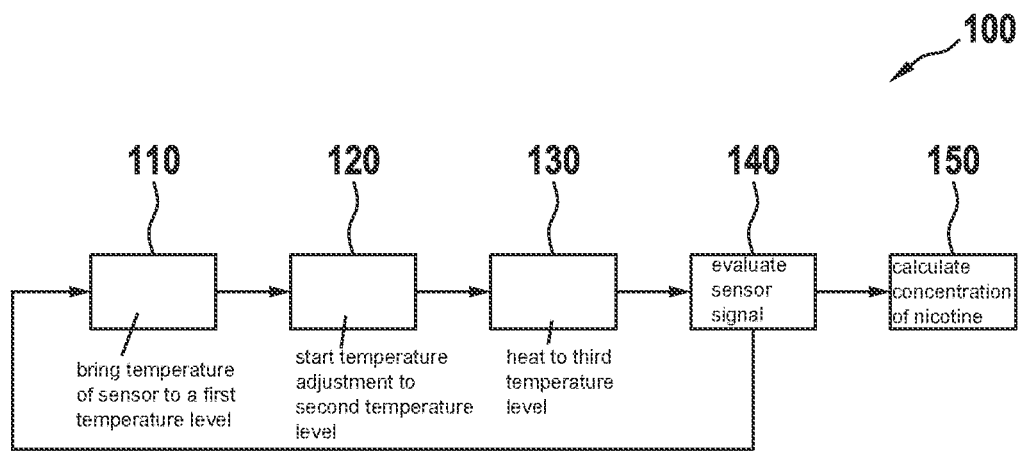
FIG. 1 shows a highly simplified flowchart of one advantageous embodiment of the method according to the present invention.

FIG. 1 schematically shows one advantageous embodiment of a method according to the present invention in the form of a highly simplified flowchart and is denoted overall by reference numeral 100.

In a first step 110 of method 100, the temperature of a sensor whose active material includes or is made up of at least one metal oxide, for example tungsten oxide, is brought to a first temperature level in a range of 200° C. to 400° C., in particular, in a range of 300° C. to 400° C., for example to a temperature level of approximately 380° C. For this purpose, for example, resistance heating, an establishment of a convection-, radiation- or ventilation-driven thermal equilibrium, a Carnot process, a Peltier effect-based process or a combination of multiple thereof may be used.

Adjusting the temperature of the sensor at such an elevated temperature causes gas species which are easily adsorbed on the active material of the sensor or absorbed thereby to desorb so that these species are cleaned off the surface of the active material. For this purpose, the first temperature level is maintained for a predetermined holding period, which is between 5 s and 120 s, for example, before step 110 is ended.

When the first temperature level has been reached and the holding period has elapsed, a temperature adjustment to a second temperature level is started in a step 120. The second temperature level may be in a range between 0° C. and 100° C., for example essentially at room temperature (approximately 20° C. to 25° C.). A temperature gradient from the first to the second temperature level is set in such a way that the corresponding transition time is between 0.1 s and 120 s, for example approximately 60 s. For temperature adjustment, in principle the same methods as in step 110 are possible, with the exception of resistance heating since this step 120 is a cooling step. When the second temperature level has been reached, the active material is maintained at this temperature level for a defined time period, for example for 1 s to 30 s. At this second temperature level, components present in the examined gas mixture may adsorb on the active material or be absorbed thereby.

As mentioned, the electrical properties of the active material depend on the chemical surroundings of the respective atoms. As a result of attached foreign species, in particular, adsorbed or absorbed gas components, the respective surface potential changes locally at the location at which the foreign species sits. If a certain foreign species is present in many locations of the active material, this effect may be measured macroscopically, i.e., at the level of the overall sensor. Since components of the gas mixture are attached to the active material of the sensor at the second temperature level, the electrical properties thereof change. In principle, a specific resistance could thus be measured at the second temperature level and be compared to a normal value for an active material to which no attaching species have been applied. A concentration of the attaching species could be inferred from the difference. This procedure, however, proves not to be selective since a wide variety of chemical compounds may be present in gas mixtures, whose effects on the electrical properties of the active material may overlap, amplify, or partially or completely compensate for one another.

As a result, in a step 130, which after the holding period at the second temperature level, heats the active material of the sensor under controlled conditions to a third temperature level. In the process, the heating rate is controlled, so that a temperature progression which is as linear as possible from the second temperature level to the third temperature level results. When using a resistive heater, it is also well-suited to operate with a linear heater voltage curve. Due to a generally non-linear relationship between the heater voltage and the temperature, temperature gradients are passed through slightly more slowly in the lower temperature range, and slightly more quickly in the higher temperature range, than the average temperature increase. The third temperature level is advantageously selected from the same temperature range as the first temperature level and, for example, is also at 380° C. The heating rate is set in step 130 in such a way that a heating duration between 1 s and 600 s results, for example 60 s. In particular, heating rates in the range of 40 K/min to 370 K/min have proven to be advantageous. During this heating step 130, components of the analyzed gas mixture attached in step 120 desorb again. This occurs as a function of the respective desorption enthalpy which may, for example, depend on a polarity of the particular species as well as their mass, in respective different temperature ranges, i.e., at different times during heating step 130. Chemical reactions, for example oxidations, reductions and/or dissociation reactions of the adsorbed or absorbed species are also possible. The fact that different components are removed at different temperatures from the active material, and thereafter are no longer able to influence its surface potential, is crucial for the measured effect on the sensor conductivity.

In this way, it is possible to examine the effects of the individual components of the gas mixture. For example, the transient electrical resistance or the transient conductivity of the active material, or the transient electrical resistance or the transient conductance of the sensor at a predetermined point in time, or at a predetermined temperature, may be evaluated for this purpose. If it is known in what temperature range the relevant compounds desorb, or despite still existing adsorption do not make a considerable contribution to the signal formation, a temperature range may be selected in each case for the detection, in which no interfering influences from other present gas components is to be feared. Within the scope of the present invention, it has been shown that, for the analysis of the nicotine content at a $WO_3$ sensor, a temperature range is particularly suitable in which the third temperature level, proceeding from the second temperature level, has been achieved 70%-100% when an average temperature gradient of approximately 370 Kelvin/minute is employed. In an evaluation step 140, the corresponding sensor signal in the explained example is thus evaluated at a point in time which is appropriately 42 s-60 s after the start of heating step 130. It shall be understood that the measurement of the transient resistance may take place both in a time-controlled manner and in a temperature-controlled manner. A temperature-controlled measurement is, in particular advantageous when the heating rate cannot be exactly controlled since a time-controlled measurement in such a case does not reliably take place in the optimal time period in which the selectivity and sensitivity of the sensor are particularly high for nicotine as the target substance.

After the measurement of the transient resistance (after reaching the third temperature level), method 100 returns back to step 110. If the first temperature level is identical to the third temperature level, step 110 may be shortened to a holding of the first temperature level over the predetermined holding period.

Parallel to the return to step 110 of method 100, in a step 150 a concentration of nicotine in the analyzed gas mixture is calculated based on the resistance ascertained in step 140. This may take place, for example, based on a calculation rule which maps the relationship between the resistance and the nicotine content, or based on tabulated values which were ascertained in calibration measurements.

In alternative embodiments of the method, a measurement of the transient resistance or of the transient conductivity may be carried out during cooling step 120, instead of or in addition to the measurement during heating step 130. This also preferably occurs at the same temperature as described above, i.e., when the second temperature level, proceeding from the first temperature level, has been achieved approximately 0%-30%. At slower average cooling rates (e.g., 10-minute cooling duration), an even lower temperature level (e.g., 30%-50%) may be used, however a stronger influence of the moisture content in the gas on the electrical conductivity then occurs.

It must be noted that the aforementioned heating and cooling rates do not have to be identical. For example, a phase in which no measurement occurs may be passed through more quickly than a phase in which a measured value is recorded. Thus, if a measurement is carried out during heating step 130, but not during cooling step 120, the latter may be designed to be shorter to increase the speed of the measurement, without having to fear disadvantages with respect to the measuring accuracy. In principle, the heating and cooling rates are only limited by the thermal inertia of the sensor.

Since each measuring cycle requires a certain time, multiple sensors operated in parallel may be resorted to increase the measuring frequency. These are preferably operated with a time offset from one another in such a case, so that the intervals between the individual measurements are, in particular, always equally long. In this way, it is possible to establish more precisely, for example, when a nicotine concentration has increased, which is advantageous, for example, when it is to be checked based on method 100 whether smoking bans are being adhered to and who is responsible for an action in violation of the ban. This may be used in company or rental car fleets, for example, so that users who do not adhere to a corresponding smoking ban may be identified and held liable. Analogously, a use in buildings, for example in hotel rooms or restaurants, is possible.

In some embodiments of the present invention, it may furthermore be provided that the result of the determination of the nicotine content is output on a display device or this information is made accessible to external recipients otherwise. If in addition, as was explained at the outset, further components of the gas mixture are analyzed, such information may also be output as a combined value which describes an air quality, for example as a numerical value, as an expressive assessment (e.g., "good," "average," "poor"), in the form of an emoticon or the like, or in the form of a color code (e.g., traffic light colors, color spectrum, etc.). For this purpose, in particular, the ascertained concentrations are converted into a quality value, for example using a characteristic diagram or another calibration, in particular, also non-linearities and/or mutual influencing of mixture components in the olfactory perception and/or possibly health-relevant threshold values being taken into consideration.

If in some particularly advantageous embodiments, as described at the outset, carbon monoxide is also analyzed, in addition to nicotine, it is possible to distinguish particularly easily between cold cigarette smell and presently burning tobacco since carbon monoxide generally does not occur in cold smoke. Moreover, a higher nicotine concentration is to be expected in the case of a presently burning cigarette. However, since the concentration may also depend on the tobacco variety, the cigarette brand, and other factors, the carbon monoxide concentration is a more reliable indicator for a discrimination between cold and fresh smoke.

Figure 2A:
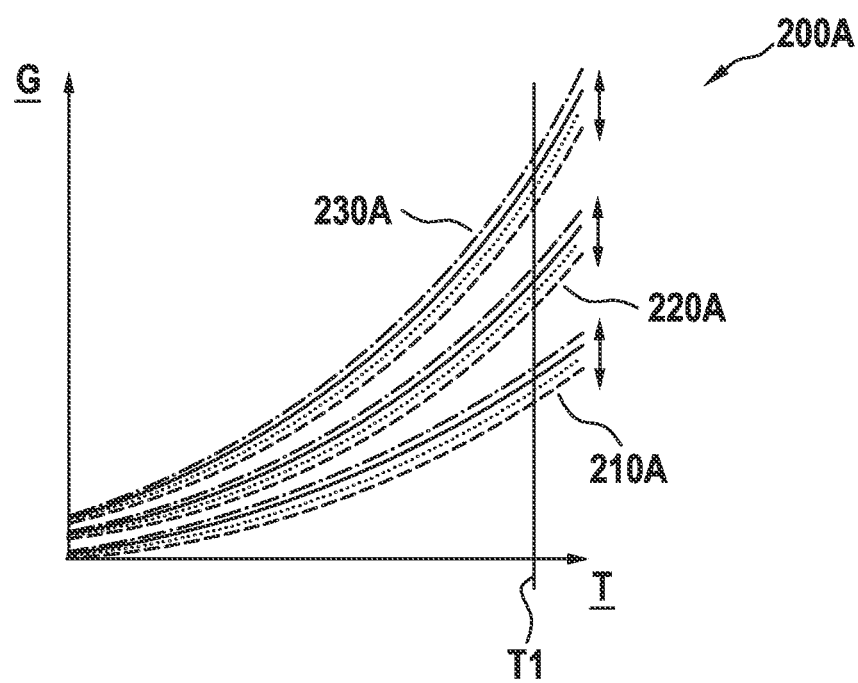

FIGS. 2A and 2B each show sensor signals based on conductivity-temperature diagrams 200A, 200B, as they may be obtained within the scope of the present invention.

Diagram 200A includes three series of curves 210A, 220A, and 230A, which each describe the development of conductivity G of the active material of the sensor used at different nicotine concentrations with temperature T. The individual curves of each series of curves 210A, 220A, 230A represent the progression for a certain gas matrix in which potential interfering gases may be present. For example, a curve of series of curves 210A may be recorded for a gas mixture which, in addition to the main components nitrogen, water vapor and oxygen, includes ethanol and possibly further immaterial components, while a further curve of series of curves 210A, in addition or instead, represents a low fraction of hydrogen sulfide in the examined gas mixture. What is crucial in the process is that, starting at a certain temperature, series of curves 210A, 220A and 230A may be reliably distinguished from one another. In the process, series of curves 210A describes the development of the conductivity without nicotine in the examined gas mixture, series of curves 220A describes it for a nicotine content of 200 ppb, and series of curves 230A describes it for a nicotine content of 500 ppb.

A temperature T1, at which the ratio between the distance of series of curves 210A, 220A, 230A from one another and the particular variance or width of the individual series of curves is optimal, is selected as the measuring point for method 100 described with respect to FIG. 1.

Diagram 200B shows in each case signal curves for the same gas mixtures as described with respect to diagram 200A. At high nicotine concentrations in the examined gas mixture, however, the sensor which was used to generate diagram 200B has a conductivity curve which does not have a monotonic increase in the dependence on the temperature. Otherwise, the explanations of the progressions of series of curves 210A, 220A, and 230A apply accordingly to the progressions of series of curves 210B, 220B, and 230B. Since series of curves 230B in the shown example has a maximum, the distance between series of curves 220B and 230B is particularly large in the surroundings of the maximum, which has a positive effect on the evaluation accuracy or robustness. Measuring point T1 is thus selected in such a way that it is situated in the vicinity of the maximum of series of curves 230B.

What is claimed is:

1. A method for determining a nicotine content in a gas mixture, comprising the following steps:

exposing a metal oxide-based sensor to the gas mixture;
applying a temperature profile over time to the metal oxide so that a temperature of the metal oxide, proceeding from a predetermined first temperature level, is brought to a predetermined second temperature level under controlled first transition conditions, and the temperature is brought from the second temperature level to a third predetermined temperature level under controlled second transition conditions;
ascertaining a transient electrical resistance of the metal oxide at at least one certain point in time during the application with the temperature profile; and
determining the nicotine content based on the ascertained resistance;
wherein the at least one certain point in time is in a time period in which the metal oxide is not present at any of the first, second, and third temperature levels.

2. The method as recited in claim 1, wherein the first and second transition conditions each encompass a transition duration and/or a temporal temperature progression of a respective temperature adjustment.

3. The method as recited in claim 2, wherein the transition duration is between 100 ms and 600 s.

4. The method as recited in claim 3, wherein the transition duration is between 1 s and 120 s.

5. The method as recited in claim 4, wherein the transition duration is between 10 s and 90 s.

6. The method as recited in claim 2, wherein each of the respective adjustments is provided by resistance heating, and/or a Carnot process, and/or convection, and/or ventilation and/or a Peltier effect.

7. The method as recited in claim 1, wherein the first temperature level is in a range of 200° C. to 400° C., the second temperature level is in a range of 0° C. to 100° C., and the third temperature level is in a range of 200° C. to 400° C.

8. The method as recited in claim 7, wherein the second temperature level is in the range of 10° C. to 40° C.

9. The method as recited in claim 8, wherein the second temperature level is in the range of 15° C. to 35° C.

10. The method as recited in claim 1, wherein the third temperature level corresponds to the first temperature level.

11. The method as recited in claim 1, wherein the certain point in time is in a time period in which the temperature is being increased in a partial time period in which a respective target temperature level, based on a difference between a starting temperature level and the target temperature level, is at least 70% achieved.

12. The method as recited in claim 1, wherein the steps of the method are repeated cyclically.

13. The method as recited in claim 1, wherein the steps of the method are repeated in parallel to each other.

14. The method as recited in claim 12, further comprising ascertaining a moving average of at least two consecutive determinations of the nicotine content.

15. The method as recited in claim 1, further comprising analyzing at least one further component of the gas mixture, the further component including carbon monoxide, and/or water vapor, and/or volatile organic compounds (VOC), and/or sulfurous compounds and/or alcohol.

16. A processing unit including a metal oxide-based sensor, the processing unit configured to determine a nicotine content in a gas mixture, the processing unit configured to:
expose the metal oxide-based sensor to the gas mixture;
apply a temperature profile over time to the metal oxide so that a temperature of the metal oxide, proceeding from a predetermined first temperature level, is brought to a predetermined second temperature level under controlled first transition conditions, and the temperature is brought from the second temperature level to a third predetermined temperature level under controlled second transition conditions;
ascertain a transient electrical resistance of the metal oxide at at least one certain point in time during the application with the temperature profile; and
determine the nicotine content based on the ascertained resistance;
wherein the at least one certain point in time is in a time period in which the metal oxide is not present at any of the first, second, and third temperature levels.

17. A non-transitory machine-readable memory medium including a computer program for determining a nicotine content in a gas mixture, the computer program, when executed by a processing unit, causing the processing unit to perform the following steps:
exposing a metal oxide-based sensor to the gas mixture;
applying a temperature profile over time to the metal oxide so that a temperature of the metal oxide, proceeding from a predetermined first temperature level, is brought to a predetermined second temperature level under controlled first transition conditions, and the temperature is brought from the second temperature level to a third predetermined temperature level under controlled second transition conditions;
ascertaining a transient electrical resistance of the metal oxide at at least one certain point in time during the application with the temperature profile; and
determining the nicotine content based on the ascertained resistance;
wherein the at least one certain point in time is in a time period in which the metal oxide is not present at any of the first, second, and third temperature levels.

* * * * *